United States Patent
Edelbrock

(10) Patent No.: US 8,273,226 B2
(45) Date of Patent: Sep. 25, 2012

(54) WEAR-RESISTANT ELECTROCHEMICAL TEST SENSOR AND METHOD OF FORMING THE SAME

(75) Inventor: Andrew J. Edelbrock, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 794 days.

(21) Appl. No.: 12/316,113

(22) Filed: Dec. 9, 2008

(65) Prior Publication Data

US 2009/0145755 A1    Jun. 11, 2009

Related U.S. Application Data

(60) Provisional application No. 61/007,087, filed on Dec. 10, 2007.

(51) Int. Cl.
*G01N 27/327*    (2006.01)

(52) U.S. Cl. .............. 204/400; 204/403.14; 204/403.02

(58) Field of Classification Search ............ 204/403.01, 204/403.04, 403.09, 403.11, 403.14, 192.3, 204/192.32, 192.1, 192.11, 400; 205/777.5, 205/778, 792; 600/345–348; 435/4–40.52; 422/68.1–98; 436/62–71, 500–548
See application file for complete search history.

(56) References Cited

U.S. PATENT DOCUMENTS

| | | | |
|---|---|---|---|
| 4,549,952 A | 10/1985 | Columbus | 204/416 |
| 4,935,346 A | 6/1990 | Phillips et al. | 325/14 |
| 5,128,015 A | 7/1992 | Szuminsky et al. | 204/403.05 |
| 5,179,005 A | 1/1993 | Phillips et al. | 435/14 |
| 5,304,468 A | 4/1994 | Phillips et al. | 435/14 |
| 5,559,065 A * | 9/1996 | Lauth et al. | 502/5 |
| 5,628,890 A | 5/1997 | Carter et al. | 204/403.05 |
| 5,723,345 A | 3/1998 | Yamauchi et al. | 436/518 |
| 5,759,364 A | 6/1998 | Charlton et al. | 204/403.14 |
| 5,789,255 A | 8/1998 | Yu | 436/95 |
| 5,798,031 A | 8/1998 | Charlton et al. | 204/403.14 |
| 5,810,725 A * | 9/1998 | Sugihara et al. | 600/372 |
| 6,132,683 A | 10/2000 | Sugihara et al. | 422/82.01 |
| 6,193,865 B1 | 2/2001 | Hodges et al. | 204/435 |
| 6,485,923 B1 | 11/2002 | Yani et al. | 435/14 |
| 6,531,040 B2 | 3/2003 | Musho et al. | 204/401 |
| 6,841,052 B2 | 1/2005 | Musho et al. | 204/401 |
| 7,118,668 B1 | 10/2006 | Edelbrock et al. | 205/777.5 |

(Continued)

FOREIGN PATENT DOCUMENTS

DE    197 47 875 A1    5/1999

(Continued)

OTHER PUBLICATIONS

PCT Search Report for International Application No. PCT/US2008/085815 dated Jun. 16, 2009 (6 pages).

(Continued)

*Primary Examiner* — Alex Noguerola
*Assistant Examiner* — Gurpreet Kaur
(74) *Attorney, Agent, or Firm* — Nixon Peabody LLP

(57) ABSTRACT

An electrochemical test sensor includes a base, a generally hard electrically-conductive layer, an electrochemically-active layer, and a lid. The electrically-conductive layer is located between the base and the electrochemically-active layer. The electrically-conductive layer and the electrochemically-active layer are made of a different material. The electrically-conductive layer and the electrochemically-active layer form an electrode pattern. The electrochemical test sensor includes a reagent adapted to assist in determining information related to an analyte of a fluid sample.

24 Claims, 6 Drawing Sheets

U.S. PATENT DOCUMENTS

| | | | |
|---|---|---|---|
| 7,122,110 B2 | 10/2006 | Deng et al. | 205/777.5 |
| 7,125,481 B2 | 10/2006 | Musho et al. | 205/777.5 |
| 2001/0042683 A1 | 11/2001 | Musho et al. | 204/403.14 |
| 2002/0175075 A1 | 11/2002 | Deng et al. | 204/403.01 |
| 2004/0149577 A1* | 8/2004 | Kumar et al. | 204/403.01 |
| 2004/0222092 A1 | 11/2004 | Musho et al. | 204/401 |
| 2005/0067280 A1* | 3/2005 | Reid et al. | 204/403.14 |
| 2006/0113187 A1 | 6/2006 | Deng et al. | 204/403.01 |
| 2006/0201805 A1* | 9/2006 | Forrow et al. | 204/403.1 |
| 2007/0202007 A1 | 8/2007 | Augstein et al. | 422/56 |

FOREIGN PATENT DOCUMENTS

| | | |
|---|---|---|
| EP | 0 851 224 B1 | 12/1997 |
| EP | 1 074 832 A1 | 2/2001 |
| EP | 0 732 406 B1 | 10/2004 |
| EP | 0 735 363 B1 | 7/2005 |
| WO | WO 2006/057722 A1 | 6/2006 |
| WO | WO 2006/103083 A1 | 10/2006 |
| WO | WO 2007/013915 A1 | 2/2007 |
| WO | WO 2007/133457 A2 | 11/2007 |

OTHER PUBLICATIONS

PCT Written Opinion for International Application No. PCT/US2008/085815 dated Jun. 16, 2009 (6 pages).

* cited by examiner

WEAR-RESISTANT ELECTROCHEMICAL TEST SENSOR AND METHOD OF FORMING THE SAME

CROSS REFERENCE TO RELATED APPLICATION

This application claims priority to application Ser.No. 61/007,087 filed on Dec. 10, 2007 which is incorporated by reference in its entirety.

FIELD OF THE INVENTION

The present invention generally relates to an electrochemical test sensor and method of forming the same. More specifically, the present invention generally relates to a method of forming a wear-resistant electrochemical test sensor that is adapted to assist in determining information related to an analyte.

BACKGROUND OF THE INVENTION

The quantitative determination of analytes in body fluids is of great importance in the diagnoses and maintenance of certain physical conditions. For example, lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used, to test a sample of blood.

A test sensor contains biosensing or reagent material that reacts with, for example, blood glucose. One type of electrochemical test sensor is a multilayer test sensor that includes a base or substrate and a lid. Another type of electrochemical test sensor includes a base, a spacer and a lid. Existing electrochemical test sensors include at least two electrodes in the form of an electrode pattern. A potential is applied across these electrodes and a current is measured at the working electrode. The current measurement is directly proportional to the size of the working electrode.

Electrodes in existing electrochemical test sensors are typically made of metallic materials that tend to be expensive. To reduce the cost, the electrodes are formed with a very thin thickness. By using thinner electrodes in a test sensor, the wear resistance of the electrodes is decreased. The practical effect of a reduced wear resistance is decreased robustness of the test sensor in processing as well as decreased robustness of the test sensor contact with the meter. This decrease in robustness also adds to the inability of these test sensors to be inserted into a meter opening more than once, while still providing an adequate contact with the meter contacts. Specifically, these thinner electrodes are also more prone to scratching during handling and insertion into the test-sensor opening of the meter. Test sensors are at least occasionally placed into a test-sensor opening more than once. For example, the user may fail to generate a useable amount of fluid before the meter times out and in such an instance, the user may reinsert the electrochemical test sensor back into the test-sensor opening of the meter instead of using a new sensor.

Therefore, it would be desirable to have an electrochemical test sensor and method of forming the same that improves the wear resistance thereof, while still being done in a cost-effective manner.

SUMMARY OF THE INVENTION

According to one embodiment, an electrochemical test sensor includes a base, a generally hard electrically-conductive layer, an electrochemically-active layer, and a lid. The electrically-conductive layer is located between the base and the electrochemically-active layer. The electrically-conductive layer and the electrochemically-active layer are made of a different material. The electrically-conductive layer and the electrochemically-active layer form an electrode pattern. The electrochemical test sensor includes a reagent adapted to assist in determining information related to an analyte of a fluid sample.

According to another embodiment, an electrochemical test sensor includes a base, a conductive layer including indium zinc oxide, indium tin oxide or the combination thereof, an electrochemically-active layer and a lid. The conductive layer is located between the base and the electrochemically-active layer. The conductive layer is made of a different material than the electrochemically-active layer. The electrochemical test sensor includes a reagent adapted to assist in determining information related to an analyte of a fluid sample.

According to one method, an electrochemical test sensor is formed and includes providing a base. A generally hard electrically-conductive layer is placed on the base. An electrochemically-active layer is placed on the generally hard electrically-conductive layer. The electrochemically-active layer is made of a different material than the generally hard electrically-conductive layer. The electrochemically-active layer and the generally hard electrically-conductive layer are formed into an electrode pattern. A second layer is applied to assist in forming a channel in the test sensor. The channel assists in allowing a fluid sample to contact a reagent located therein.

According to another method, an electrochemical test sensor is formed and includes providing a base. An electrochemically-active material and rhodium are co-sputtered on the base. The electrochemically-active material and rhodium are formed into an electrode pattern. A second layer is applied to assist in forming a channel in the test sensor. The channel assists in allowing a fluid sample to contact a reagent located therein.

According to a further embodiment, an electrochemical test sensor includes a base, an electrochemically-active layer, carbon material and a lid. The electrochemically-active layer is located between the base and the carbon material. The electrochemically-active layer is made of a different material than carbon. The electrochemically-active layer forms an electrode pattern. The electrochemically-active layer and the carbon material form a plurality of test-sensor contacts configured to establish contact with a meter. The electrochemical test sensor includes a reagent adapted to assist in determining information related to an analyte of a fluid sample.

BRIEF DESCRIPTION OF THE DRAWINGS

FIG. 1b is a side view of the electrochemical test sensor of FIG. 1a.

FIG. 1c is a top view of the base to be used in the electrochemical test sensor of FIG. 1a.

FIG. 2b is a side view of the electrochemical test sensor of FIG. 2a.

FIG. 5b is a side view opposite of the channel of the electrochemical test sensor of FIG. 5a.

FIG. 6b is a side view of the electrochemical test sensor of FIG. 6a.

DETAILED DESCRIPTION OF ILLUSTRATED EMBODIMENTS

The present invention is directed to a method of improving the wear resistance of an electrochemical test sensor, while still producing a test sensor in a cost-effective manner. More specifically, it is desirable for the present invention to improve the usability of the electrochemical test sensor by allowing a user to insert the test sensor at least twice into the test-sensor opening, if necessary, during the process of obtaining information of the fluid analyte. The electrochemical test sensor would also desirably have adequate contact with the meter contacts.

The electrochemical test sensors are adapted to receive a fluid sample and be analyzed using an instrument or meter. The test sensor assists in determining information related to the analytes such as analyte concentrations. Analytes that may be measured include glucose, cholesterol, lipid profiles, microalbumin, urea, creatinine, creatine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

In one embodiment, the electrochemical test sensor includes at least a base, a generally hard electrically-conductive layer, an electrochemically-active layer and a second layer such as a lid and/or a spacer. The generally hard electrically-conductive layer is made of a different material than the electrochemically-active layer. In one embodiment, the electrochemical test sensors include a base, a generally hard electrically-conductive layer, an electrochemically-active layer and a lid. In another embodiment, the electrochemical test sensors include a base, a generally hard electrically-conductive layer, an electrochemically-active layer, a spacer and a lid.

The base, spacer and lid may be made from a variety of materials such as polymeric materials. Non-limiting examples of polymeric materials that may be used to form the base, spacer and lid include polycarbonate, polyethylene terephthalate (PET), polystyrene, polyimide, and combinations thereof. It is contemplated that the base, spacer and lid may be independently made of other materials. The electrode pattern may be made from a variety of conductive materials including, but not limited to, gold, platinum, rhodium, palladium, ruthenium, carbon or combinations thereof.

Figure 1A:
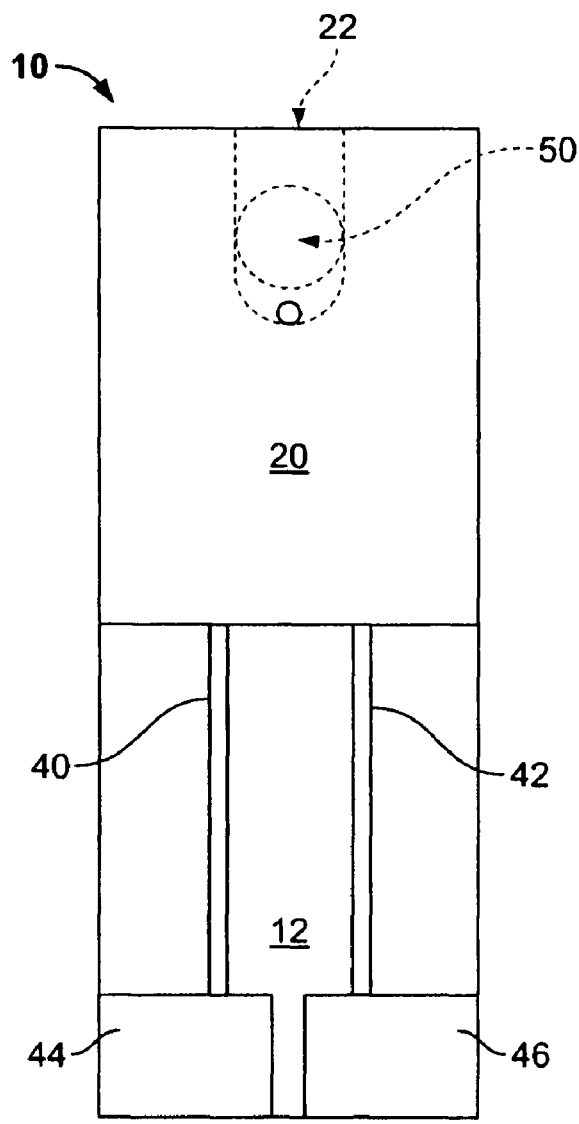
FIG. 1a is a top view of an electrochemical test sensor according to one embodiment.
Figure 1B:
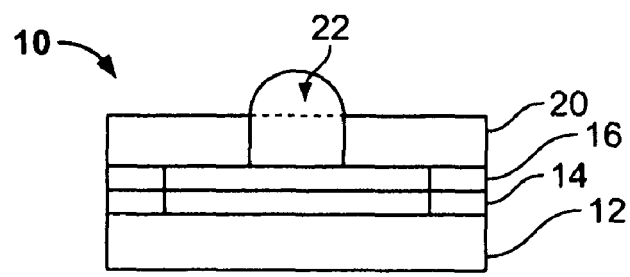
Figure 1C:
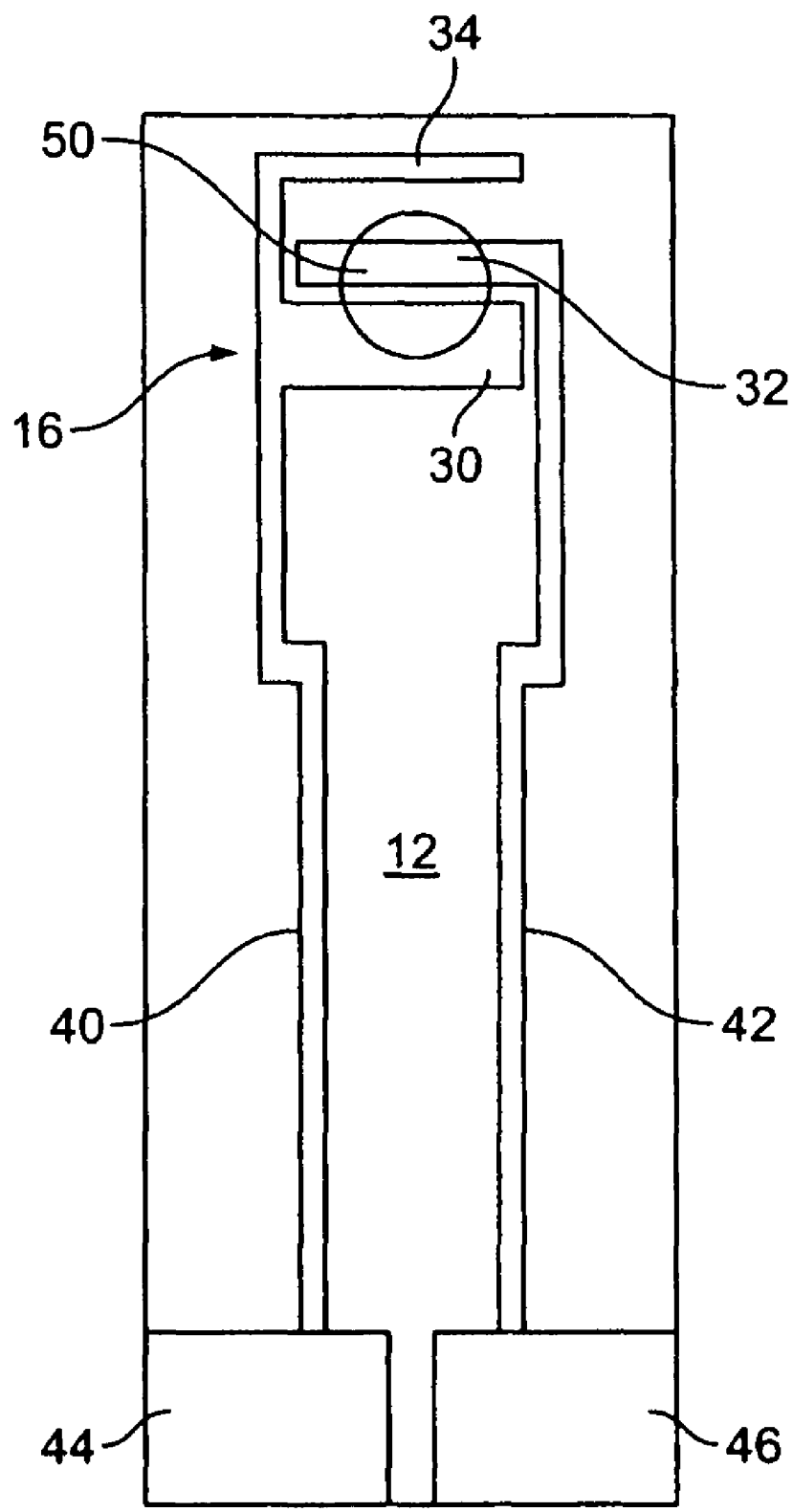

One non-limiting example of an electrochemical test sensor is shown in FIGS. 1a-1d. FIGS. 1a, 1b depict an electrochemical test sensor 10 that includes a base 12, a generally hard electrically-conductive layer 14, an electrochemically-active layer 16, and a lid 20. FIG. 1c depicts the generally hard electrically-conductive layer 14, and the electrochemically-active layer 16 without a lid. Referring back to FIG. 1b, a channel 22 (e.g., capillary channel) is formed when the base 12, the generally hard electrically-conductive layer 14, the electrochemically-active layer 16 and the lid 20 are attached to each other. The capillary channel 22 provides an enclosed flow path for introducing the sample into the test sensor 10 and eventually contacting the electrodes 30, 32, 34 and, thus, forms a reaction zone.

As shown in FIG. 1a, the test sensor 10 includes a reactive or fluid-receiving area 50 that contains an enzyme. The enzyme is selected to react with the desired analyte or analytes to be tested so as to assist in determining an analyte concentration of a fluid sample. The reactive area 50 includes a reagent for converting an analyte of interest (e.g., glucose) in a fluid test sample (e.g., blood) into a chemical species that is electrochemically measurable, in terms of the electrical current it produces, by the components of the electrode pattern.

The reagent typically contains an enzyme (e.g., glucose oxidase), which reacts with an analyte (e.g., glucose) and with an electrochemical mediator (e.g., ferricyanide) to produce an electrochemically measurable species that can be detected by the electrodes. The reactive area 50 may comprise a polymer, an enzyme, and an electron acceptor. The reactive area 50 also may include additional ingredients such as a buffer and a surfactant in some embodiments of the present invention. It is contemplated that other enzymes may be used to react with glucose such as glucose dehydrogenase. One type of glucose dehydrogenase is FAD-GDH. If the concentration of another analyte is to be determined, an appropriate enzyme is selected to react with the analyte.

The generally hard electrically-conductive layer may be made from a variety of materials. It is highly desirable for little or no interference between the generally hard electrically-conductive layer, the reagent (e.g., mediator and/or enzyme) and/or electrochemically-active layer. In other words, the generally hard electrically-conductive layer is desirably very compatible with the reagent system. For example, in one embodiment, the generally hard electrically-conductive layer is indium zinc oxide (IZO). In another embodiment, the generally hard electrically-conductive layer is indium tin oxide (ITO). IZO and ITO may be obtained from commercially available sources. It is contemplated that other materials may be used in forming the generally hard electrically-conductive layer.

In one example, the indium zinc oxide (IZO) may be used with a reagent system that includes a glucose dehydrogenase (e.g., FAD-GDH) enzyme using a mediator such as ferricyanide, a 3-phenylimino-3H-phenothiazine or a 3-phenylimino-3H-phenoxazine. One example of such a mediator is 3-(2',5'disulfophenylimino)-3H-phenothiazine.

The generally hard electrically-conductive layer 14 and the electrochemically-active layer 16 form a plurality of electrodes 30, 32, 34, a plurality of conductive leads or traces 40, 42, and test-sensor contacts 44, 46. Thus, in this embodiment the electrode pattern is formed from two distinct layers. The plurality of electrodes of FIG. 1c includes at least a counter electrode 30 and a working electrode 32 according to this embodiment. The working electrode measures the current when a potential is applied across the working and counter electrodes. The counter electrode should be sufficiently large so as to support the reaction occurring at the working electrode. The applied voltage may be referenced to the reagent deposited adjacent to the counter electrode. The conductive leads 40, 42 assist in establishing electrical communication between the electrodes and the test-sensor contacts 44, 46. The test-sensor contacts 44, 46 are electrically connected with meter contacts (not shown) and assist in conveying information of the analyte to the meter to assist in, for example, determining the analyte concentration.

It is contemplated that the areas forming the conductive leads and test-sensor contacts may be enlarged from that shown in FIGS. 1a, 1c. For example, the conductive leads and test-sensor contacts may be only separated by a thin area with the rest of the base being covered by the electrically-conductive layer and the electrochemically-active layer.

Other electrodes such as a trigger electrode 34 are shown in FIG. 1c. It is contemplated that other electrodes may be used. For example, an electrochemical test sensor may include a detection electrode that detects an underfill condition. The electrochemical test sensor may also include a hematocrit electrode that assists in correcting for the bias that occurs with selected hematocrit concentrations. Additional electrodes include, but are not limited to, electrodes that detect other analytes or species that may potentially interfere with the measurement of the desired analyte. Also, a second working electrode that assists in determining the concentration of another analyte may be used.

It is contemplated that more or less electrodes may be formed in the electrochemical test sensor. For example, the electrochemical test sensor may include exactly two electrodes or at least three electrodes. The exactly two electrodes may be a working electrode and a counter electrode in which an electrochemically created current flow when these electrodes are electrically connected and a potential is created between them. The electrodes are formed of conductive materials such as, for example, metallic materials (e.g., gold, platinum, palladium, rhodium, ruthenium, or combinations thereof) or carbon.

Figure 2A:
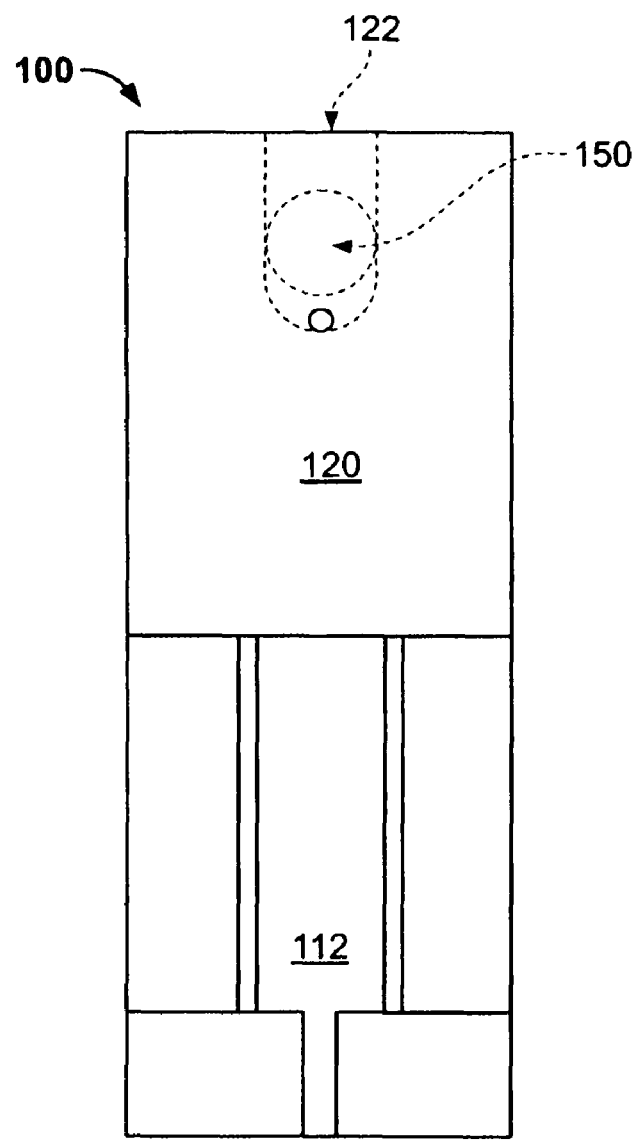
FIG. 2a is a top view of an electrochemical test sensor according to another embodiment.
Figure 2B:
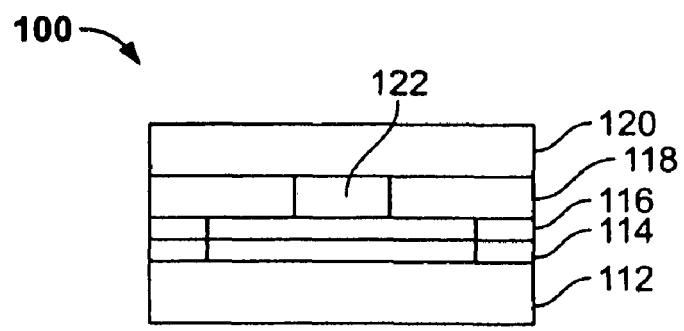

Another non-limiting example of an electrochemical test sensor is shown in FIGS. 2a, 2b. FIGS. 2a, 2b depict an electrochemical test sensor 100 that includes a base 112, a generally hard electrically-conductive layer 114, an electrochemically-active layer 116, a spacer 118 and a lid 120. The base 112, the generally hard electrically-conductive layer 114 and the electrochemically-active layer 116 may be the same or similar to the respective base 12, the generally hard electrically-conductive layer 14 and the electrochemically-active layer 16 discussed above. A channel 122 (e.g., capillary channel) is formed when the base 112, the generally hard electrically-conductive layer 114, the electrochemically-active layer 116, the spacer 118 and the lid 120 are attached to each other. The capillary channel 122 provides an enclosed flow path for introducing the sample into the test sensor 100 and eventually contacting the electrodes and, thus, forms a reaction zone.

The electrodes formed on the base 112 may be the same as described above with respect to the base 12. The electrodes include a counter and working electrode in one embodiment. In other embodiments, the electrodes may include additional electrodes such as the above discussed trigger electrode, detection electrode, hematocrit electrode, a second working electrode and other electrodes.

In one method, the electrochemical test sensors may be formed from ribbon strips. The ribbon strips may be made from processes such as a multiple-sheet process or a web process. For example, in an embodiment with a base, generally hard electrically-conductive layer, an electrochemically-active layer, spacer and lid, a base-ribbon strip, a spacer-ribbon strip and a lid-ribbon strip may be used. For improved efficiency, the electrochemical test sensors are generally formed after all of the ribbon strips have been attached.

According to one method, an electrochemical test sensor is formed. A base is provided and a generally hard electrically-conductive layer is placed on the base. The generally hard electrically-conductive layer may be placed on the base by, for example, sputtering. An electrochemically-active layer is placed on the generally hard electrically-conductive layer. The electrochemically-active layer is made of a different material than the generally hard electrically-conductive layer. The electrochemically-active layer, as well as the generally hard electrically-conductive layer, is formed into an electrode pattern. A second layer is applied to assist in forming a channel in the test sensor. The channel assists in allowing a fluid sample to contact a reagent located therein.

The electrode pattern is generally from about 50 to about 500 Angstroms (Å) in thickness and, more typically, from about 150 to about 350 Angstroms (Å) in thickness. The electrochemically-active layer may be located on the generally hard electrically-conductive layer using, for example, physical vapor deposition (e.g., sputtering), coating, chemical vapor deposition (cvd), plating or printing.

The electrode pattern may be defined by using a mask and a laser such as, for example, an Excimer laser, solid state, YAG (singled, doubled or tripled frequency) or a carbon dioxide-based laser. One example of a mask is a chrome-on-glass mask in which a beam of light is only allowed to pass through selected areas.

According to another method, the electrode pattern may be formed with a laser using direct writing of the lines. In a method using a laser with direct writing of the lines, a laser beam of light is moved so as to define the electrode pattern. The laser may define, for example, the plurality of electrodes, the conductive leads and the meter contacts. Lasers that produce a beam of energy capable of removing a layer and that can be moved to form an electrode pattern may be used in this method. Non-limiting examples of such lasers are carbon dioxide-based lasers and all yttrium-based lasers such as yttrium aluminum garnet (YAG) lasers.

In one process, the reagent may be applied to the electrode surfaces. The reagent may be applied to the electrode surface by, for example, gravure or screen printing, microdepositing (e.g., ink-jet spraying) and coating (e.g., slot coating). In any embodiment, the reagent would need to contact the fluid sample, such as by using a capillary channel.

At least one of the base, generally hard electrically-conductive layer, and the electrochemically-active layer is then attached to a second layer. In one embodiment, the second layer is a lid. As discussed above, the lid may be in the form of a ribbon strip. In another embodiment, the second layer is a spacer. As discussed above, the spacer may be in the form of a ribbon strip. According to another embodiment, the second layer may be a spacer-lid combination. The spacer-lid combination may be in the form of a ribbon strip (combination of spacer-ribbon strip and lid-ribbon strip) that has been previously formed before being attached to form an electrochemical test sensor. If ribbon strips are used, the test sensors may be excised using a mechanical punch or other methods.

The second layer (e.g., lid or spacer) may be attached to the base/electrode structure using, for example, a pressure-sensitive adhesive and/or a hot melt adhesive. Thus, the attachment uses pressure, heat or the combination thereof. It is contemplated that other materials may be used to attach the second layer and the base/electrode structure. It is also contemplated that the second layer and the base/electrode structure may be attached using ultrasonic energy or solvent welding.

In another process, a method of forming an electrochemical test sensor includes providing a base. Electrochemically-active material and rhodium are co-sputtered on the base. For example, an electrochemically-active material such as gold is co-sputtered with rhodium. The electrochemically-active material with rhodium is then formed into an electrode pattern. A second layer is applied to assist in forming a channel in the test sensor. As discussed above, the second layer may be a lid or a spacer. The channel assists in allowing a fluid sample to contact a reagent located therein. By including rhodium, such a process improves the wear resistance of the electrochemical test sensor. The rhodium is also desirable because of its compatibility with many mediators and enzymes such as, for example, FAD-GDH (glucose dehydrogenase) enzyme and mediators such as ferricyanide, a 3-phenylimino-3H-phenothiazine or a 3-phenylimino-3H-phenoxazine.

Figure 3:
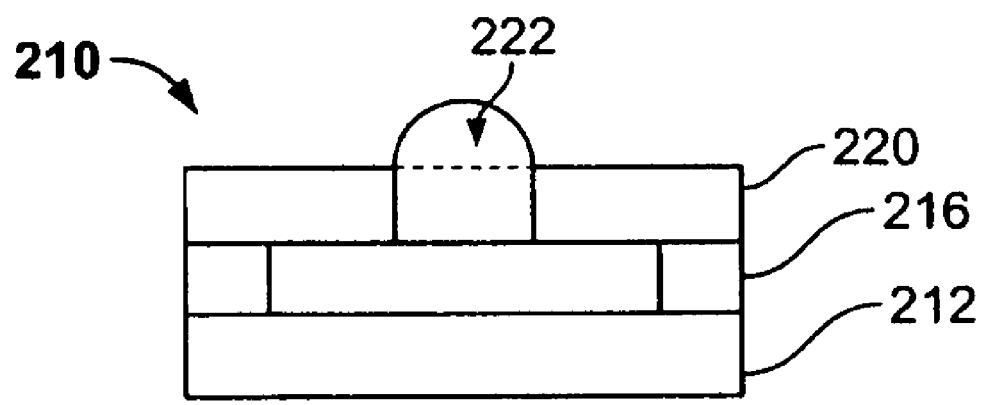
FIG. 3 is a side view of the electrochemical test sensor according to another embodiment.

One non-limiting example of an electrochemical test sensor using electrochemically-active material and rhodium is shown in FIG. 3. FIG. 3 depicts an electrochemical test sensor 210 that includes a base 212, electrochemically-active/rhodium material 216 and a lid 220. Referring still to FIG. 3, a channel 222 (e.g., capillary channel) is formed when the base 212, the electrochemically-active/rhodium material 216 and the lid 220 are attached to each other. The capillary channel 222 provides an enclosed flow path for introducing the sample into the test sensor 210 and eventually contacting the plurality of electrodes and, thus, forms a reaction zone. The plurality of electrodes may be the same or similar to that described above with respect to FIGS. 1a-1d.

Figure 4:
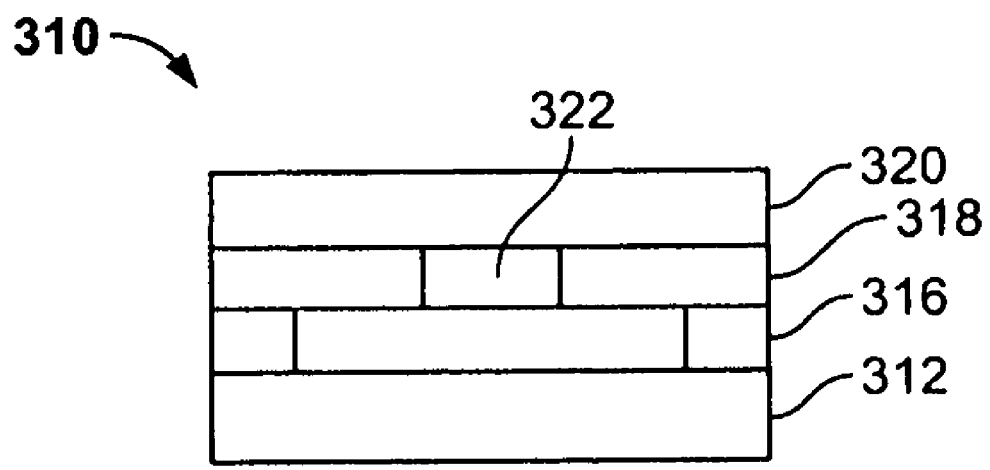
FIG. 4 is a side view of the electrochemical test sensor of FIG. 3a with a spacer.

It is also contemplated that an electrochemical test sensor using electrochemically-active material and rhodium may include a spacer and a lid. For example, FIG. 4 depicts an electrochemical test sensor 310 including a base 312, electrochemically-active/rhodium material 316, a spacer 318 and a lid 320. A channel 322 (e.g., capillary channel) is formed when the base 312, the electrochemically-active/rhodium material 316, the spacer 318 and the lid 320 are attached to each other. The plurality of electrodes may be the same or similar to that described above with respect to FIGS. 1a-1d.

In another process, a method of forming an electrochemical test sensor includes providing a base. An electrochemically-active layer is placed on a base and carbon material (e.g., a carbon layer) is placed over the electrochemically-active layer where the meter contacts will connect when inserted into the meter. In this embodiment, the electrochemically-active layer is formed of a different material than the carbon material. The electrochemically-active material forms the electrode pattern, while the electrochemically-active material and carbon form the test-sensor contacts that are configured to establish contact with the meter. A second layer is applied to assist in forming a channel in the test sensor. As discussed above, the second layer may be a lid or a spacer. The channel assists in allowing a fluid sample to contact a reagent located therein. By including carbon, such a process improves the wear resistance of the electrochemical test sensor.

Figure 5A:
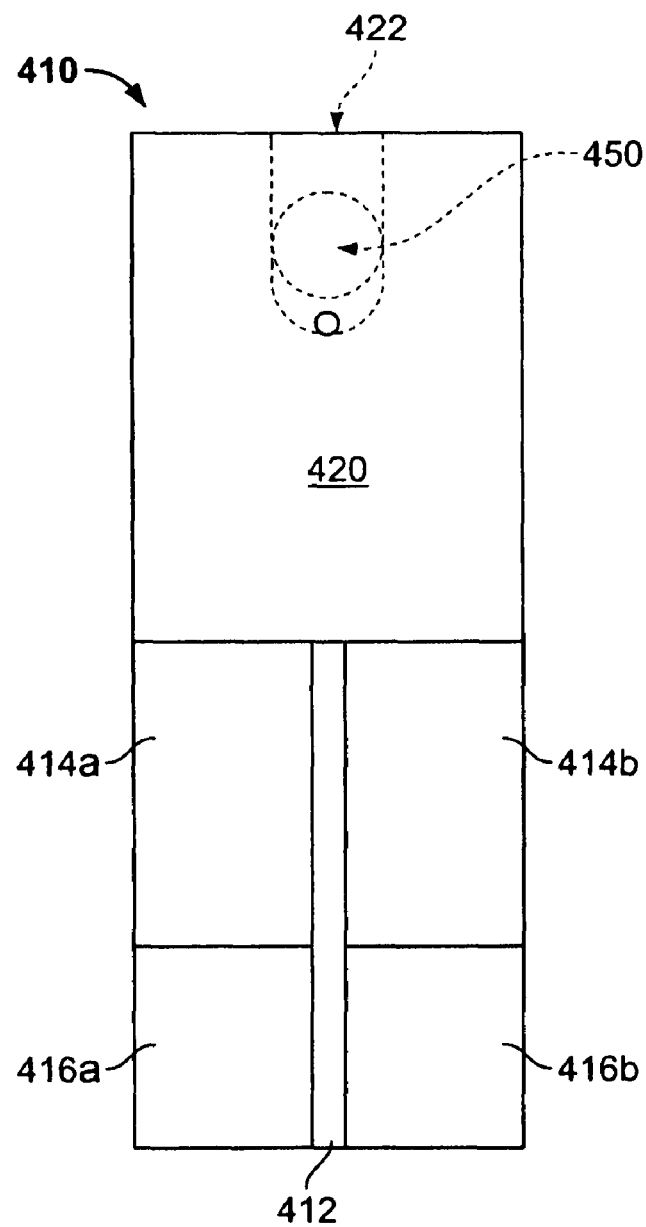
FIG. 5a is a top view of the electrochemical test sensor according to a further embodiment.
Figure 5B:
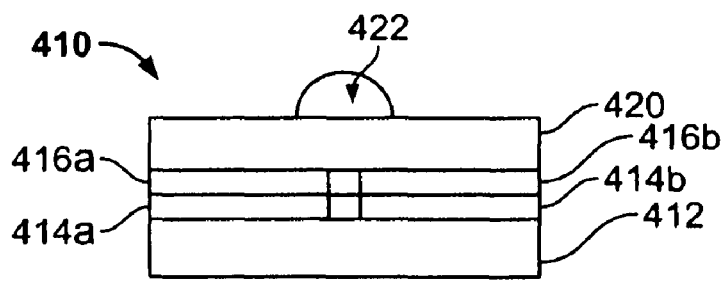

One non-limiting example of an electrochemical test sensor using an electrochemically-active layer and carbon material is shown in FIGS. 5a, 5b. FIGS. 5a, 5b depict an electrochemical test sensor 410 that includes a base 412, electrochemically-active layer 414, carbon material 416, a lid 420 and a reactive area 450. The electrochemically-active layer 414 forms the plurality of electrodes (e.g., at least a working electrode and counter electrode), test-sensor contacts/conductive leads 414a, 414b. The carbon material 416 forms test-sensor contacts 416a, 416b and assists in protecting the electrochemically-active layer at the test-sensor contacts. It is contemplated that the carbon material may extend over a wider area than depicted in FIG. 5a. A channel 422 (e.g., capillary channel) is formed when the base 412, the electrochemically-active layer 414 and the lid 420 are attached to each other in this embodiment. The plurality of electrodes may be the same or similar to that described above with respect to FIGS. 1a-1d.

Figure 6A:
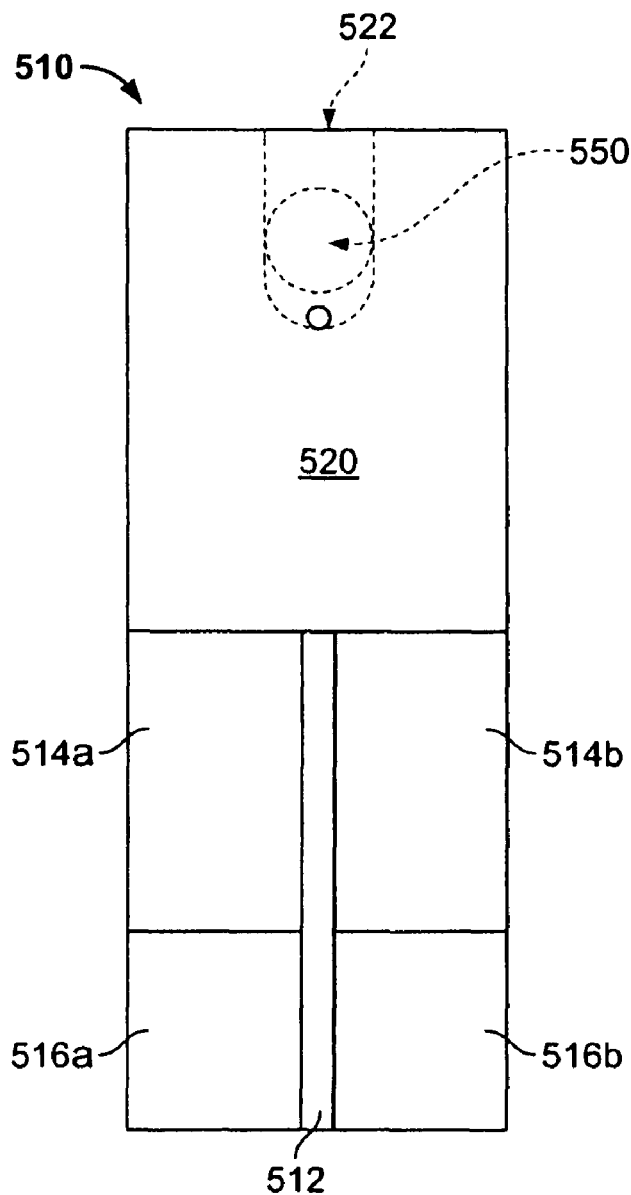
FIG. 6a is a top view of the electrochemical test sensor according to yet another embodiment.
Figure 6B:
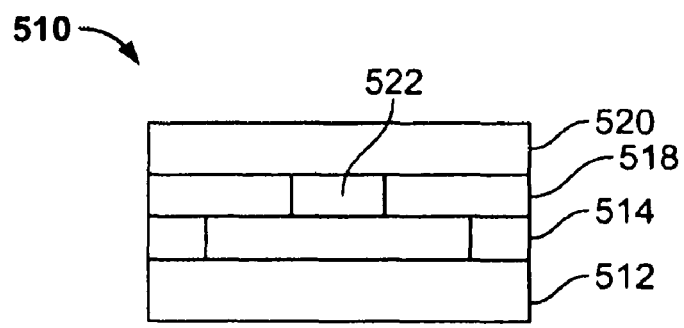

It is also contemplated that an electrochemical test sensor using an electrochemically-active layer and carbon material may include a spacer and a lid. For example, FIGS. 6a, 6b depict an electrochemical test sensor 510 including a base 512, electrochemically-active layer 514, carbon material 516, a spacer 518 and a lid 520. The electrochemically-active layer 514 forms the plurality of electrodes (e.g., at least a working electrode and counter electrode), test-sensor contacts/conductive leads 514a, 514b. The carbon material 516 forms test-sensor contacts 516a, 516b and assists in protecting the electrochemically-active layer at the test-sensor contacts. It is contemplated that the carbon material may extend over a wider area than depicted in FIG. 6a. A channel 522 (e.g., capillary channel) is formed when the base 512, the electrochemically-active layer 514, the spacer 518 and the lid 520 are attached to each other. The plurality of electrodes may be the same or similar to that described above with respect to FIGS. 1a-1d.

Embodiment A

An electrochemical test sensor comprising a base, a generally hard electrically-conductive layer, an electrochemically-active layer, and a lid, the generally hard electrically-conductive layer being located between the base and the electrochemically-active layer, the generally hard electrically-conductive layer and the electrochemically-active layer being made of a different material, the generally hard electrically-conductive layer and the electrochemically-active layer forming an electrode pattern, and wherein the electrochemical test sensor includes a reagent adapted to assist in determining information related to an analyte of a fluid sample.

Embodiment B

The test sensor of alternative embodiment A further including a spacer, the spacer and the lid assisting in forming a channel in which to receive the fluid, the channel including the reagent.

Embodiment C

The test sensor of alternative embodiment A wherein the electrochemically-active layer includes gold, platinum, rhodium, palladium, ruthenium or combinations thereof.

Embodiment D

The test sensor of alternative embodiment A wherein the reagent includes glucose oxidase or glucose dehydrogenase.

Embodiment E

An electrochemical test sensor comprising a base, a conductive layer including indium zinc oxide, indium tin oxide or the combination thereof, an electrochemically-active layer and a lid, the conductive layer being located between the base and the electrochemically-active layer, the conductive layer being made of a different material than the electrochemically-active layer and wherein the electrochemical test sensor includes a reagent adapted to assist in determining information related to an analyte of a fluid sample.

Embodiment F

The test sensor of alternative embodiment E further including a spacer, the spacer and the lid assisting in forming a channel in which to receive the fluid, the channel including the reagent.

Embodiment G

The test sensor of alternative embodiment E wherein the electrochemically-active layer includes gold, platinum, rhodium, palladium, ruthenium or combinations thereof.

Embodiment H

The test sensor of alternative embodiment E wherein the reagent includes glucose oxidase or glucose dehydrogenase.

Process I

A method of forming an electrochemical test sensor, the method comprising the acts of:
  providing a base;
  placing a generally hard electrically-conductive layer on the base;

placing an electrochemically-active layer on the generally hard electrically-conductive layer, the electrochemically-active layer being made of a different material than the generally hard electrically-conductive layer;

forming the electrochemically-active layer and the generally hard electrically-conductive layer into an electrode pattern; and applying a second layer to assist in forming a channel in the test sensor, the channel assisting in allowing a fluid sample to contact a reagent located therein.

Process J

The method of alternative process I wherein the generally hard electrically-conductive layer includes indium zinc oxide, indium tin oxide or the combination thereof.

Process K

The method of alternative process I wherein the forming of the electrode pattern includes the use of laser-ablating.

Process L

The method of alternative process I wherein the second layer is a lid.

Process M

The method of alternative process I wherein the second layer is a spacer and further includes applying a lid to the spacer so as to define the channel, the spacer being located between the lid and the base.

Process N

The method of alternative process M wherein the channel is a capillary channel.

Process O

The method of alternative process I wherein the electrode pattern is formed by printing, coating, vapor deposition, sputtering or electrochemical deposition.

Process P

A method of forming an electrochemical test sensor, the method comprising the acts of:

providing a base;

co-sputtering an electrochemically-active material and rhodium on the base;

forming the electrochemically-active material and rhodium into an electrode pattern; and applying a second layer to assist in forming a channel in the test sensor, the channel assisting in allowing a fluid sample to contact a reagent located therein.

Process Q

The method of alternative process P wherein the forming the electrochemically-active material and rhodium into an electrode pattern includes the use of laser-ablating.

Process R

The method of alternative process P wherein the second layer is a lid.

Process S

The method of alternative process P wherein the second layer is a spacer and further includes applying a lid to the spacer so as to define the channel, the spacer being located between the lid and the base.

Process T

The method of alternative process S wherein the channel is a capillary channel.

Embodiment U

An electrochemical test sensor comprising a base, an electrochemically-active layer, carbon material and a lid, the electrochemically-active layer being located between the base and the carbon material, the electrochemically-active layer being made of a different material than carbon, the electrochemically-active layer forming an electrode pattern, the electrochemically-active layer and the carbon material forming a plurality of test-sensor contacts and wherein the electrochemical test sensor includes a reagent adapted to assist in determining information related to an analyte of a fluid sample.

Embodiment V

The test sensor of alternative embodiment U further including a spacer, the spacer and the lid assisting in forming a channel in which to receive the fluid, the channel including the reagent.

Embodiment W

The test sensor of alternative embodiment U wherein the electrochemically-active layer includes gold, platinum, rhodium, palladium, ruthenium or combinations thereof.

Embodiment X

The test sensor of alternative embodiment U wherein the reagent includes glucose oxidase or glucose dehydrogenase.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. An electrochemical test sensor comprising a base, a conductive layer comprising indium tin oxide, an electrochemically-active layer, and a lid, the conductive layer being located between the base and the electrochemically-active layer, the conductive layer and the electrochemically-active layer being made of a different material, the conductive layer and the electrochemically-active layer forming a plurality of electrodes, a plurality of conductive leads and a plurality of test-sensor contacts, and wherein the electrochemical test sensor includes a reagent adapted to assist in determining information related to an analyte of a fluid sample.

2. The test sensor of claim 1, further including a spacer, the spacer and the lid assisting in forming a channel in which to receive the fluid, the channel including the reagent.

3. The test sensor of claim 1, wherein the electrochemically-active layer includes gold, platinum, rhodium, palladium, ruthenium or combinations thereof.

4. The test sensor of claim 1, wherein the reagent includes glucose oxidase or glucose dehydrogenase.

5. An electrochemical test sensor comprising a base, a conductive layer including indium zinc oxide, an electrochemically-active layer and a lid, the conductive layer being located between the base and the electrochemically-active layer, the conductive layer being made of a different material than the electrochemically-active layer, the conductive layer and the electrochemically-active layer forming a plurality of electrodes, a plurality of conductive leads and a plurality of test-sensor contacts, and wherein the electrochemical test sensor includes a reagent adapted to assist in determining information related to an analyte of a fluid sample.

6. The test sensor of claim 5, further including a spacer, the spacer and the lid assisting in forming a channel in which to receive the fluid, the channel including the reagent.

7. The test sensor of claim 5, wherein the electrochemically-active layer includes gold, platinum, rhodium, palladium, ruthenium or combinations thereof.

8. The test sensor of claim 5, wherein the reagent includes glucose oxidase or glucose dehydrogenase.

9. A method of forming an electrochemical test sensor, the method comprising the acts of:

providing a base;

placing a conductive layer on the base, the conductive layer including indium tin oxide;

placing an electrochemically-active layer on the conductive layer, the electrochemically-active layer being made of a different material than the conductive layer;

forming the electrochemically-active layer and the conductive layer into a plurality of electrodes, a plurality of conductive leads and a plurality of test-sensor contacts; and applying a second layer to assist in forming a channel in the test sensor, the channel assisting in allowing a fluid sample to contact a reagent located therein.

10. The method of claim 9, wherein the forming of the plurality of electrodes includes the use of laser-ablating.

11. The method of claim 9, wherein the second layer is a lid.

12. The method of claim 9, wherein the second layer is a spacer and further includes applying a lid to the spacer so as to define the channel, the spacer being located between the lid and the base.

13. The method of claim 12, wherein the channel is a capillary channel.

14. The method of claim 9, wherein the plurality of electrodes is formed by printing, coating, vapor deposition, sputtering or electrochemical deposition.

15. The method of claim 9, wherein the electrochemically-active layer includes gold, platinum, rhodium, palladium, ruthenium or combinations thereof.

16. The method of claim 9, wherein the reagent includes glucose oxidase or glucose dehydrogenase.

17. A method of forming an electrochemical test sensor, the method comprising the acts of:

providing a base;

placing a conductive layer on the base, the conductive layer including indium zinc oxide;

placing an electrochemically-active layer on the conductive layer, the electrochemically-active layer being made of a different material than the conductive layer;

forming the electrochemically-active layer and the conductive layer into a plurality of electrodes, a plurality of conductive leads and a plurality of test-sensor contacts; and applying a second layer to assist in forming a channel in the test sensor, the channel assisting in allowing a fluid sample to contact a reagent located therein.

18. The method of claim 17, wherein the forming of the plurality of electrodes includes the use of laser-ablating.

19. The method of claim 17, wherein the second layer is a lid.

20. The method of claim 17, wherein the second layer is a spacer and further includes applying a lid to the spacer so as to define the channel, the spacer being located between the lid and the base.

21. The method of claim 20, wherein the channel is a capillary channel.

22. The method of claim 17, wherein the plurality of electrodes is formed by printing, coating, vapor deposition, sputtering or electrochemical deposition.

23. The method of claim 17, wherein the electrochemically-active layer includes gold, platinum, rhodium, palladium, ruthenium or combinations thereof.

24. The method of claim 17, wherein the reagent includes glucose oxidase or glucose dehydrogenase.

* * * * *